United States Patent [19]

van der Lely et al.

[11] Patent Number: 5,018,669
[45] Date of Patent: May 28, 1991

[54] SPREADER FOR SPREADING GRANULAR AND/OR POWDERY MATERIAL

[75] Inventors: Ary van der Lely, Maasland; Cornelis J. G. Bom, Rozenburg, both of Netherlands

[73] Assignee: C. van der Lely N.V., Maasland, Netherlands

[21] Appl. No.: 35,075

[22] Filed: May 1, 1979

[30] Foreign Application Priority Data

May 5, 1978 [NL] Netherlands ............... 7804824
Mar. 1, 1979 [NL] Netherlands ............... 7901632

[51] Int. Cl.$^5$ ............................... A01C 17/00
[52] U.S. Cl. .................... 239/665; 239/670; 239/682; 239/684; 239/687
[58] Field of Search ........... 239/661, 665, 670, 676, 239/687, 683, 684, 682

[56] References Cited

U.S. PATENT DOCUMENTS

| | | |
|---|---|---|
| 2,652,261 | 9/1953 | Presler . |
| 2,723,860 | 11/1955 | Weeks ........................ 239/661 |
| 3,109,657 | 11/1963 | Dreyer ....................... 239/665 |
| 3,133,737 | 5/1964 | Kaller . |
| 3,313,549 | 4/1967 | Bell .......................... 239/682 X |
| 3,539,113 | 11/1970 | Tyler . |
| 3,558,065 | 1/1971 | van der Lely ................. 239/683 |
| 3,586,246 | 6/1971 | van der Lely et al. .......... 239/665 |
| 3,652,019 | 3/1972 | van der Lely ................. 239/682 |
| 3,767,126 | 10/1973 | van der Lely ................. 239/661 |
| 3,899,138 | 8/1975 | van der Lely et al. .......... 239/661 |
| 4,205,793 | 6/1980 | van der Lely ................. 239/661 |

FOREIGN PATENT DOCUMENTS

| | | |
|---|---|---|
| 496523 | 7/1977 | Australia . |
| 251940 | 1/1967 | Austria . |
| 258628 | 12/1967 | Austria . |
| 729496 | 3/1966 | Canada . |
| 781829 | 4/1968 | Canada . |
| 802764 | 12/1968 | Canada . |
| 896411 | 3/1972 | Canada . |
| 901037 | 5/1972 | Canada . |
| 1992777 | 7/1964 | Fed. Rep. of Germany . |
| 1996423 | 5/1967 | Fed. Rep. of Germany . |
| 1965463 | 8/1967 | Fed. Rep. of Germany . |
| 1966951 | 8/1967 | Fed. Rep. of Germany . |
| 1988403 | 6/1968 | Fed. Rep. of Germany . |
| 1990601 | 8/1968 | Fed. Rep. of Germany . |
| 1993246 | 9/1968 | Fed. Rep. of Germany . |
| 1995258 | 10/1968 | Fed. Rep. of Germany . |
| 1457772 | 1/1970 | Fed. Rep. of Germany . |
| 1457870 | 6/1970 | Fed. Rep. of Germany . |
| 7115099 | 8/1971 | Fed. Rep. of Germany . |
| 2011894 | 4/1972 | Fed. Rep. of Germany . |
| 2215155 | 10/1972 | Fed. Rep. of Germany . |
| 2344346 | 3/1975 | Fed. Rep. of Germany . |
| 1945076 | 12/1978 | Fed. Rep. of Germany . |
| 2818227 | 11/1979 | Fed. Rep. of Germany . |
| 2917843 | 11/1979 | Fed. Rep. of Germany . |
| 391691 | 11/1908 | France . |
| 1440385 | 4/1966 | France . |
| 1523961 | 3/1968 | France . |

(List continued on next page.)

*Primary Examiner*—Andres Kashnikow
*Attorney, Agent, or Firm*—Penrose Lucas Albright

[57] ABSTRACT

A spreader for spreading granular and/or powdery materials having a hopper and rotary distribution members with ejection blades on plates located below the hopper. The areas covered by the two distribution members can be adjusted so that they substantially coincide with one another. In some embodiments, the orientation of the ejection blades on the plates can be adjusted. Material flows to the distribution members through feeding means that include outlet openings and ports that can be in register with the openings. Also, displacers or closing members for affecting this flow can be positioned near the outlets at the lower portion of the hopper. A transmission, including change speed gears, can be connected through endless flexible members, i.e., ropes or belts to the shafts mounting the distribution members.

11 Claims, 7 Drawing Sheets

SPREADER FOR SPREADING GRANULAR AND/OR POWDERY MATERIAL

SUMMARY OF THE INVENTION

According to a first aspect of the present invention there is provided a spreader for spreading granular or powdery material or both, comprising at least two distribution members which are drivable in rotation about upwardly extending rotary axes, feeding means being provided for supplying material to the distribution members so that each of the two distribution members receives material at a location offset from the rotary axis of the distribution member, the distribution members, being drivable in opposite senses such that their regions of nearest approach move in a direction opposite the general direction in which the material is ejected from the distribution members during operation, the feeding means being constructed and arranged to feed material to the distribution members during operation in such a way that the areas covered by the respective distribution members substantially coincide with one another.

Since the two distribution members spread the material over the same area, any irregularities of distribution by the two distribution members will balance one another so that the net result is a more uniform distribution pattern. Therefore, the spreader will, for example, be less sensitive to the action of the wind. Moreover, material of irregular structure will be spread more uniformly. Furthermore, several kinds of material can be spread more uniformly without needing special adjustments.

Two outlet ports may be provided near the distribution member at a small distance from one another, subtending together an angle of about 60° at the rotary axis of the distribution member. This has a favorable effect on the uniform distribution of the material across a wide strip of land during operation.

The distribution members may have ejection blades of substantially identical structure. Thus the spreader can have a simple construction, while the distribution members spread the material in the same manner. Preferably each of the distribution members provides a channel, the bottom of which is constituted by a slightly curved plate which is located in a curved plane parallel to the rotary axis of the distribution member, the top side of the plate being provided with an upper rim extending forwardly with respect to the direction of rotation of the distribution member. The plate will support the material over a given height and eject it as a layer of defined thickness. This is conducive to uniformity of distribution, the material ejected by one distribution member being less likely to come into contact with that ejected by the other distribution member.

The distribution members are preferably coupled with a transmission mechanism enabling the rotary speed of the distribution members to be varied. By regulating the speed of the distribution members, the width of spread of the material can be readily adjusted, particularly where the two distribution members spread the material across the same sector.

According to a second aspect of the present invention there is provided a spreader for spreading granular or powdery material, comprising a distribution member, which is rotatable about a rotary axis, and a hopper in which a displacer is arranged, the displacer being connected with the distribution member to lead an ejection blade of the distribution member, with respect to the direction of operative rotation of the distribution member so that the flow of material from the hopper through an outlet port during operation is affected by the displacer and uniformly passes to the distribution member.

According to a third aspect of the present invention there is provided a spreader for spreading granular and/or powdery material, comprising a hopper having at least one outlet port and a distribution member which is rotatable about a rotary axis and is provided with an ejection member, the distribution member being connected with a closing member which alternately opens and closes the outlet port of the hopper during rotation of the distribution member.

According to a fourth aspect of the present invention there is provided a spreader for spreading granular or powdery material or both and comprising at least two distribution members which, in operation, spread material over a substantially common area.

According to a fifth aspect of the present invention there is provided a spreader for spreading granular or powdery material or both and comprising a distribution member which has an adjustable ejection blade.

For a better understanding of the present invention and to show how it may be carried into effect, reference will now be made, by way of example only, to the accompanying drawings, in which:

DESCRIPTION OF THE PREFFERRED EMBODIMENTS

Figure 1:
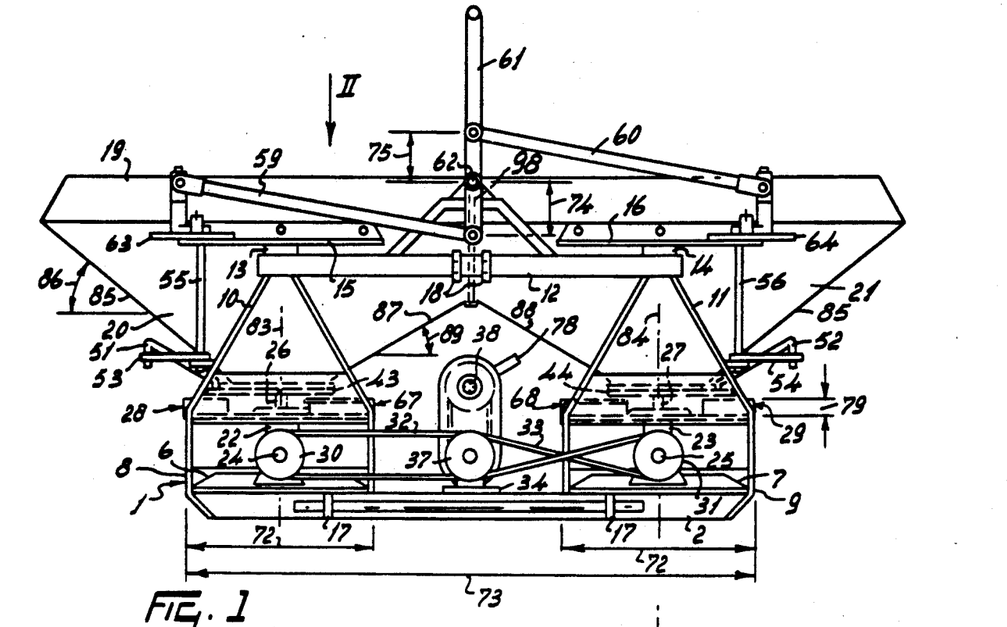
FIG. 1 is a front view of a spreader.
Figure 2:
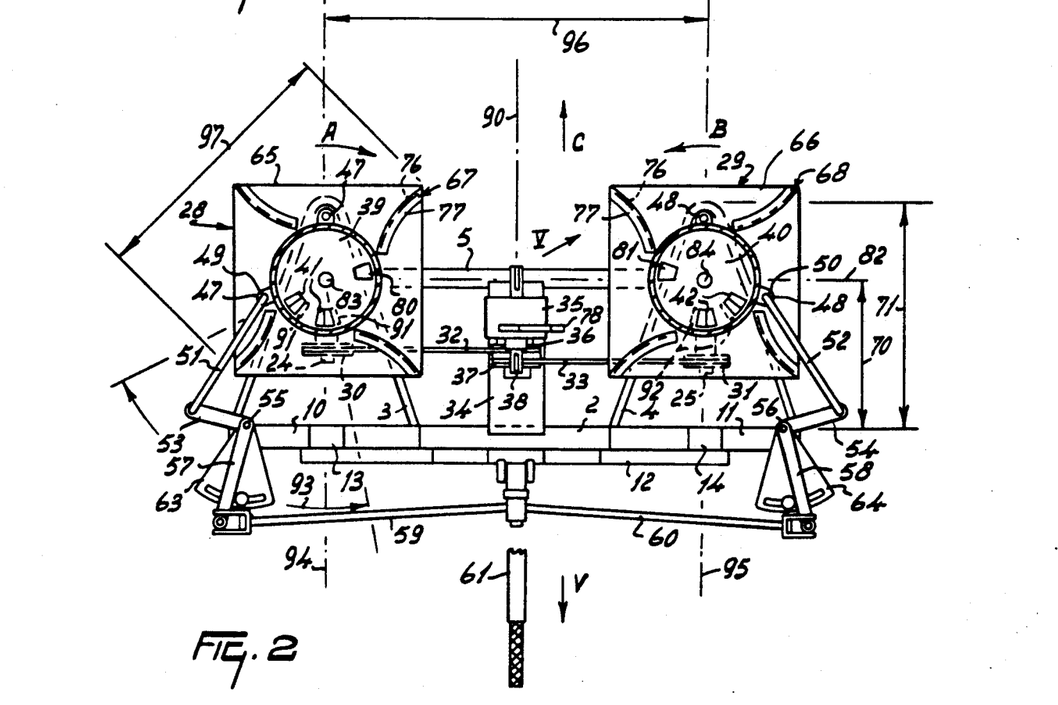
FIG. 2 is a plan view of part of the spreader of FIG. 1 taken in the direction of the arrow II in FIG. 1, some parts being omitted.

FIGS. 1 and 2 illustrate a spreader for spreading granular or powdery material or both which, in this case, is a fertilizer distributor. This fertilizer distributor comprises a frame 1 having a lowermost frame beam 2 extending transversely of the intended direction V of operative travel.

From the plan view of FIG. 2 it can be seen that the frame beam 2 is connected near each of its ends with a V-shaped carrier 3 and 4, the apices of these carrierspointing towards the rear with respect to the direction V. The two carriers 3 and 4 are interconnected by means of a frame beam 5, which is located at the level of and behind the frame beam 2. The frame beam 5 is parallel to the frame beam 2 and the distance 70 between them is about two thirds of the distance 71 between the apices of the carriers 3 and 4 and the frame beam 2. The carriers 3 and 4 have a width 72 where they meet the frame beam 2, this width 72 being about one third of the length 73 of the frame beam 2. Between the limbs of each carrier 3 and 4 and in line with the frame beam 5 there is a frame beam 6 or 7 which interconnects the two limbs of the carrier 3 or 4.

Attached to the frame beam 2 are two frame portions 8 and 9, each of which has two limbs which are parallel over part of their length and then converge. The parallel parts of the limbs of the frame portions 8 and 9 are vertical and are secured to the beam 2 where the carriers 3 and 4 meet the frame beam 2. The convergent parts 10 and 11 of the limbs of the frame portions 8 and 9 are at the top of the parallel portions and are interconnected by a frame beam 12. The frame beam 12 is located almost directly above the frame beam 2. Near its ends the frame beam 12 has two supports 13 and 14 on its top surface, each support having a horizontal plate 15 and 16.

The frame 1 has coupling points for attaching it to a three-point lifting device of a tractor. Thus the frame beam 2 has two coupling points 17, and the frame beam 12 has a coupling point 18. The frame 1 carries a hopper 19 having two funnel portions 20 and 21.

The frame beams 6 and 7 each have a gear box 22 and 23 respectively. Each of the gear boxes 22 and 23 has an input shaft 24 and 25 respectively, projecting horizontally and substantially forwardly, and a vertical output shaft 26 and 27 respectively. Distribution members 28 and 29 respectively are connected to the output shafts 26 and 27. The input shafts 24 and 25 are provided with pulleys 30 and 31 respectively. These pulleys can be rotated by means of ropes or belts 32 and 33 respectively. The frame 1 has a transmission mechanism mounted on a support 34 and comprising a change-speed mechanism 35. The transmission mechanism comprises two pulleys 36 and 37 arranged on the change-speed mechanism 35. The change-speed mechanism 35 has an input shaft 38, which can be connected by an auxiliary shaft with the power take-off shaft of a tractor to which the distributor is hitched, so that the input shaft 38 is driven by the tractor. The belts 32 and 33 pass around the pulleys 30 and 36, 31 and 37 respectively so that the distribution members 28 and 29 are driven in opposite senses as indicated by the arrows A and B in FIG. 2. The distribution members are driven so that the regions of nearest approach to each other move in a direction opposite the general direction of distribution of material. This mean distribution direction is indicated by an arrow C. In other words the distribution members 28 and 29 move at their regions of nearest approach in the direction V. The change-speed gear 35 is not shown in detail in this embodiment but is capable of varying the speed of the pulleys 36 and 37 and hence the speed of rotation of the distribution members 28 and 29.

Each of the funnel portions 20 and 21 of the hopper 19 has a bottom wall 39 and 40 respectively having two outlet ports 41 and 42 respectively. These outlet ports can be opened to a greater or lesser extent by slides 43 and 44 provided beneath the walls 39 and 40. The slides 43 and 44, like the bottom walls 39 and 40, are circular plates and they each have two apertures 91 and 92 respectively, the size and location of which correspond to those of the ports 41 and 42 respectively. The slides 43 and 44 are rotatable about the centerlines 83 and 84 of the shafts 26 and 27. The outlet ports 41 and 42 are located so that the distribution members spread the material across two substantially coinciding sectors. This means that the locations of the ports 41 and 42 are chosen so that, as viewed in the direction V the left-hand boundary of the sector covered by the left-hand distribution member 29 almost coincides with the left-hand boundary of the sector covered by the right hand distribution member, and conversely the right-hand boundary of the right-hand sector almost coincides with the right-hand boundary of the left-hand sector. It should be noted that the two distribution members are located at the same vertical level. The slides 43 and 44 may be displaced by means of an adjusting mechanism so that the outlet ports 41 and 42 are opened and closed in unison. This means that the slides 43 and 44 are simultaneously turned through the same angles but in opposite senses about the shafts 26 and 27. For this purpose each slide has a lug 47 and 48 respectively having an aperture 49 and 50 respectively. In these apertures is pivotally arranged one end of a rod 51 and 52 respectively. The other end of these rods are pivotally connected to levers 53 and 54 respectively, which are fixed to vertical pivotal shafts 55 and 56 respectively. The shafts 55 and 56 are rotatably arranged on the frame portions 8 and 9 and the plates 15 and 16 respectively. At the top each shaft 55 and 56 has a lever 57 and 58 respectively which is pivotally connected with rods 59 and 60 respectively. The rods 59 and 60 are pivotally connected to a common actuating arm 61, which can turn about a horizontal shaft 62. The rod 59 connects arm 61 below shaft 62 and the rod 60 below it. The distances 74 and 75 between the pivotal connections and the shaft 62 are equal to one another. Near the levers 57 and 58 the plates 15 and 16 carry sectors 63 and 64 respectively, which indicate the set position of the slides 43 and 44 with respect to the outlet ports 41 and 42 respectively. The parts 51 to 62 together constitute the adjusting mechanism for the slides 43 and 44. The bottom walls 39 and 40 and the slides 43 and 44 with the ports 41, 80 and 91, 42, 81 and 92 respectively constitute feeding means for feeding material from the hopper to the distribution members. These parts are located above the distribution members as is shown in the Figures.

Each of the distribution members 28 and 29 comprises in this embodiment a square, flat plate 65 and 66 respectively, each provided with four ejection blades 67 and 68 respectively. The ejection blades 67 and 68 have identical shapes to one another and have gutter-shaped or L-shaped vertical crosssections. The flat plates 65 and 66 are perpendicular to the rotary axes 83 and 84. Each blade comprises a curved wall 76 which stands perpendicular to its plate 65 or 66 and therefore parallel to the rotary axes 83 and 84. The top edges of the walls 76 have rims 77 which project forwards with respect to the direction of rotation A or B.

It has been found that the distributor described above is particularly suitable for spreading grains, particularly grains of fairly hard consistency. It has been found that during operation, the distribution pattern is obtained despite the fact that the distribution members are located at the same vertical level and the two sections covered overlap one another considerably; this might give rise to the supposition that grains ejected by one of the two distribution members would collide with those ejected by the other and that the distribution pattern would consequently be distorted. Contrary to these expectations, the distribution pattern is, however, particularly satisfactory.

The width of the distribution pattern can be adjusted in a simple manner by varying the speed of rotation of the distribution members. It is desirable for the speed of the distribution members to be at the most about 750 rev/min, whereas at the least it should be about 300 rev/min. The width of the overall sector covered by the two distribution members 28 and 29 may vary slightly with different kinds of material. A material of larger grain size will be ejected further than a material of a smaller grain size. Irrespective of the kind of material, it will be spread uniformly across the overall width, since any variation of the distribution pattern of different kinds of materials spread by one distribution member will be balanced out by a variation of the distribution pattern of the material spread by the other distribution member. Therefore, the distributor can be very satisfactorily used for spreading different kinds of materials, for example, fertilizers. To alter the distribution width, the transmission ratio of the transmission mechanism can be changed by the change-speed mechanism 35. To this end the change-speed mechanism 35 has an adjusting member 78. If a different kind of material is to be spread across the same width as another material during a run of the distributor, the speed of the two distribution members can be adjusted accordingly. In order to obtain an effective spread of the material it is advantageous for the two ports 41 and 42 to subtend an angle 93 of about 60° at the rotary axis 83 and 84 respectively. If only one outlet port is provided in the bottom wall 39 and 40 respectively, the angle that it subtends is preferably not smaller than 15° to 20°. In this embodiment the angle 93 is about 70°. Further ports 80 and 81 are provided between the axes 83 and 84 near the vertical plane 82 containing these rotary axes. The ports 41 and 42 are located in front of this plane 82, viewed in the direction V. The ports 41 and 42 are located almost wholly on the outboard sides of the vertical planes 94 and 95 extending in the direction V and containing the axes 83 and 84 respectively. One of each pair of ports 41 and 42 is located near the plane 94 and 95 respectively.

Figure 3:
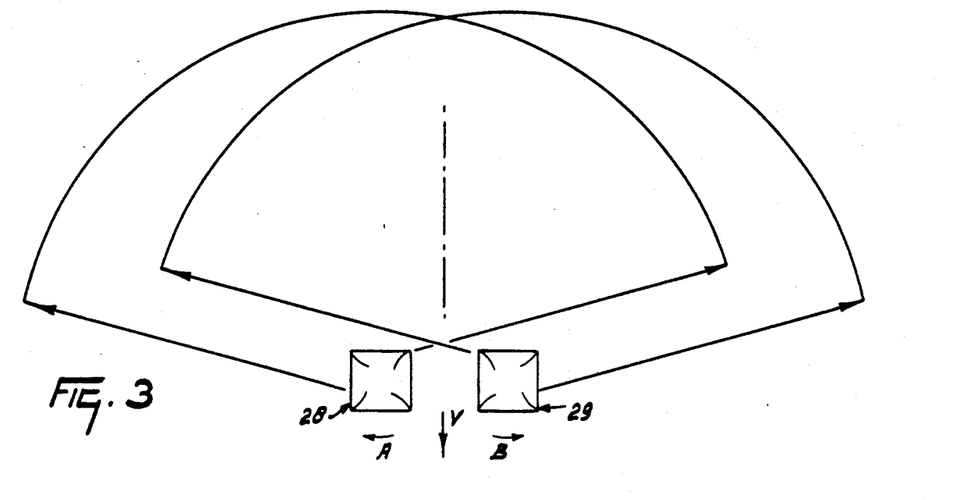
FIG. 3 is a schematic plan view of the distribution pattern for the spreader of FIGS. 1 and 2.

The distribution of the material by the two distribution members over coinciding sectors is enhanced when the distance 96 between the planes 94 and 95 is smaller that 2.5 times the distance 97 between the diametrically opposite radially outermost parts of the distribution members 28 and 29. In the embodiment shown in FIGS. 1 to 3 the distance 96 is about 1.5 times the distance 97.

Figure 5:
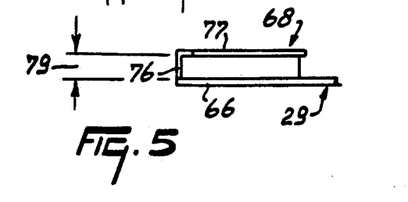
FIG. 5 is an enlarged elevational view of part of the spreader taken in the direction of the arrow V in FIG. 2.
Figure 6:
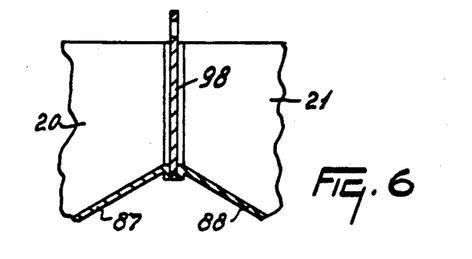
FIG. 6 shows on an enlarged scale another part of the spreader of FIGS. 1 and 2.

The shape of the ejection blades 67 and 68 of the distribution members 28 and 29 respectively is such that the risk of collision of grains of material ejected by one distribution member with those ejected by the other distribution member is minimized. To this end the upwardly extending curved wall 76 of each blade has a height 79 (FIG. 5) of, for example, not less than 1.5 centimeters and not more than 5 centimeters. In this embodiment the height is about 3 centimeters. The material flowing from the outlet ports to the distribution members is engaged by the ejection blades and will cover the wall 76 over its full height so that each distribution member ejects the material in a layer, the vertical thickness of which depends upon the height 79 of the walls 76. Since each of the distribution members ejects material in a layer of a given width, the grains will leave the distribution members with lower density than if they all left the distribution members in a common horizontal plane. Since the grains of material are ejected in a thicker layer of lower density, the grains ejected by the distribution members are more likely to pass one another without colliding.

Figure 4:
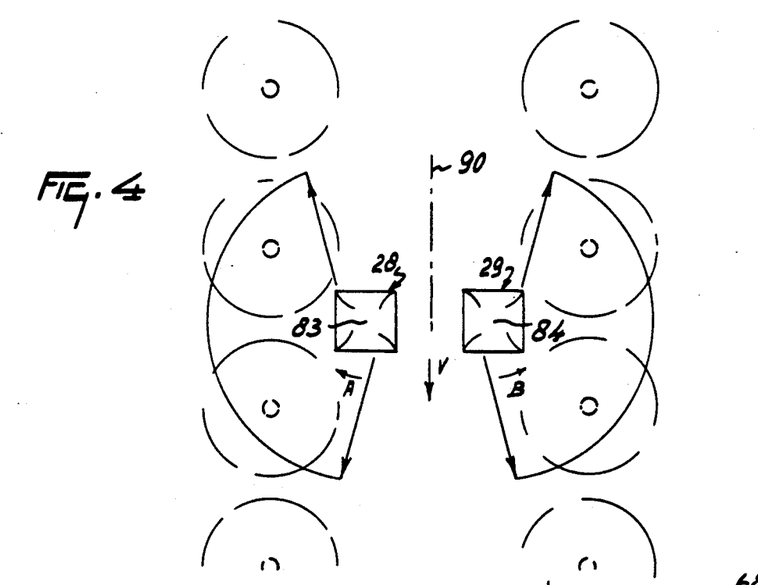
FIG. 4 is a schematic plan view of an alternative distribution pattern of the spreader of FIGS. 1 and 2.

Each of the bottom walls 39 and 40 of the funnel portions 20 and 21 has, as already mentioned, a further outlet port 80 and 81 respectively. These ports 80 and 81 are located (FIG. 2) just behind the vertical plane 82. The ports 80 and 81 are located on the inboard sides of the axes 83 and 84. The slides 43 and 44 can be turned, in a manner not shown, about the shafts 26 and 27 respectively so that they co-operate with the ports 80 and 81, while the ports 41 and 42 remain closed. The material will thus arrive on the plates 65 and 66 of the distribution members 28 and 29 respectively at different positions, compared with material falling through the ports 41 and 42. The material is thus spread by each of the distribution members in a different direction. When the ports 80 and 81 are used, each of the distribution members will spread laterally of the distributor as is illustrated schematically in FIG. 4. Thus the material is spread by each of the distribution members over a separate sector. In this way the distributor can distribute material over separate strips of soil; this is useful, for example, in row cultures such as in orchards. The distance between each of the two strips and the vertical plane 90 going through the longitudinal center line of the device can be adjusted by varying the rotary speed of the two distribution members. If the speed of the distribution members is raised, the material will be thrown slightly farther so that the material is spread over strips of soil spaced further apart than with a lower rotary speed of the distribution members.

In this embodiment the change-speed mechanism 35 is designed so that it can vary the rotary speed of the two distribution members while the rotary speeds of the distribution members remain equal to one another. However, the driving gear for each of the distribution members may be provided with transmission means capable of driving the distribution members, if desired, with unequal speeds. This may be useful for ejecting the material further with one distribution member than with the other. Thus one distribution member may cover a strip of land located on one side the distributor nearer the plane 90 than the strip of land on the other side of said plane covered by the other distribution member. Except in peculiar circumstances, it is usually desirable to drive the distribution members with equal speeds, when they spread the material across the same sector in order to cover a broad strip of land with material as is shown schematically in FIG. 3.

The distributor is particularly suitable for spreading granular material. In order to maximize the capacity of the hopper and hence to minimize the frequencey of refilling during operation, the walls 85 are at the smallest possible angle 86 to the horizontal at which the flow of the granular material down the hopper walls towards the outlet ports is still guaranteed. The adjoining walls 87 and 88 may be arranged at a smaller angle 89 to the horizontal. In this embodiment the angle 89 is about 30°, whereas the angle 86 is about 40°.

So that the slides 43 and 44 can be set either with the two ports 91 and 92 co-operating with the two outlet ports 41 and 42 respectively or with one of the ports 91 and 92 co-operating with the further outlet ports 80 and 81, each of the slides is provided with two tags 47 and 48 having apertures 49 and 50 respectively. The slides 43 and 44 can thus be connected with the coupling rods 51 and 52 in two different positions about the axes 83 and 84. In the positions shown in FIG. 2 the two ports 91 and 92 in the slides 43 and 44 co-operate with the ports 41 and 42, while the further outlet ports 80 and 81 are closed by the slides.

During operation the material is carried in the hopper 19, from which it falls to the distribution members. The part of the hopper located above the funnel portions 20 and 21 may be divided by means of a removable partition 98. During spreading of the material, this may have the advantage that it can be assessed whether the left-hand side and the right-hand side of the hopper are emptying at the same rate. This indicates whether each of the distribution members is ejecting material at the same rate, this usually being desirable. The partition 98 may furthermore be used, for example, for spreading two kinds of material simultaneously. Thus from one hopper part on one side of the partition 98 one kind of material can be fed to one of the distribution members, whereas from the other hopper part a different kind of material can be fed to the other distribution member.

Figure 7:
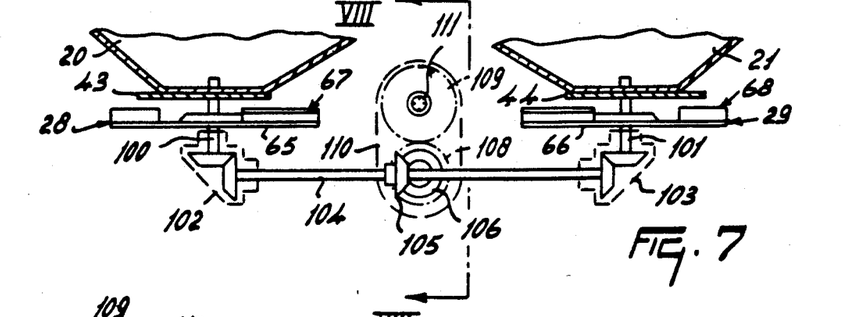
FIG. 7 shows schematically an alternative transmission mechanism for a spreader as shown in FIG. 1.
Figure 8:
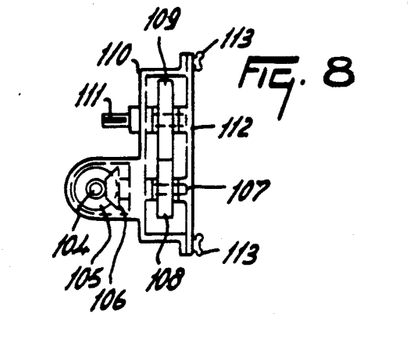
FIG. 8 is a section view taken on the line VIII—VIII in FIG. 7.

FIGS. 7 and 8 show a further embodiment of the transmission mechanism for the distribution members 28 and 29 for a distributor as shown in FIGS. 1 and 2. FIGS. 7 and 8 show the parts concerned only schematically. The parts corresponding with those of FIGS. 1 and 2 are designated by the same reference numerals as in those Figures. In the embodiment shown in FIGS. 7 and 8 the distribution members 28 and 29 are arranged on vertical shafts 100 and 101 journalled in gear boxes 102 and 103 respectively. The gear boxes 102 and 103, which may be mounted on the carrier frames 3 and 4, are intercoupled by a driving shaft 104, to which a bevel pinion, housed in a gear box 110, is fastened. The gear box 110 may be mounted on the support 34. The pinion 105 is in mesh with a pinion 106 on a shaft 107 journalled in the gear box 110. The shaft 107 is provided with a spur pinion 108 forming a change pinion which meshes with a change pinion 109 on a shaft 111 journalled in the gear box 110. The shaft 111 constitutes an input shaft for the gear box 110, like the shaft 38 of FIGS. 1 and 2, and can be coupled by an auxiliary shaft with the power take-off shaft of a tractor or a similar vehicle to which the distributor is hitched. The gear box 110 has a cover plate 112 fastened by wing nuts 113 to the box 110. After releasing the wing nuts, the cover plate can be removed from the box and the pinions 108 and 109 interchanged or replaced by other meshing pinions to alter the speed of rotation of the distribution members with the same speed of the input shaft 111. The drive of the distribution members by means of pinions has the advantage that the speed can be kept constant, since no slip will occur between the various transmission elements. A constant rotary speed of the distribution members 28 and 29, and usually equal speeds for both of them, are conducive to a uniform distribution pattern.

Figure 9:
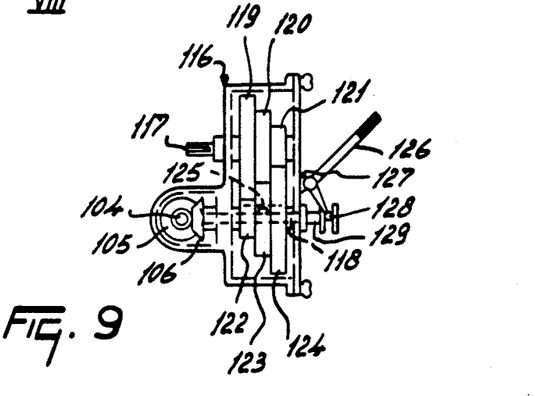
FIG. 9 shows an alternative arrangement for the parts visible in FIG. 8.

FIG. 9 shows a different embodiment of a gear box by means of which the speed of the distribution members 28 and 29 can be changed. FIG. 9 shows a gear box 116, the upper region of which supports a shaft 117, serving as an input shaft like the shaft 111. In the lower region a shaft 118 is provided, which performs the same function as the shaft 107 of the preceding embodiment. The shaft 118 is provided with a bevel pinion 106 co-operating with the bevel pinion 105 on the shaft 104. The shaft 117 is provided with three pinions 119, 120, 121 of different diameters. The shaft 118 has three pinions 122, 123 and 124 also of different diameters, which are in mesh with respective ones of the pinions 119 to 121 as is shown in FIG. 9. The pinions 119 to 121 are rigidly secured to the shaft 117, whereas the pinions 122 to 124 are rotatable about the shaft 118. By means of a displaceable key 125 (shown schematically) any one of the three pinions 122 to 124 can be selected and coupled with the shaft 118. The key 125 can be adjusted by means of a lever 126, which is pivotally arranged on a support 127 and is connected through a coupling 128 with a key carrier 129. For adjusting the speed of the shaft 118 and hence of the distribution members 28 and 29 a connection can be established between any one of the pinions 122 to 124 and the shaft 118. Thus the drive from the shaft 117 is transmission through that one of the pinions 119 to 121 which meshes with the selected pinion of the set of pinions 122 to 124.

Figure 10:
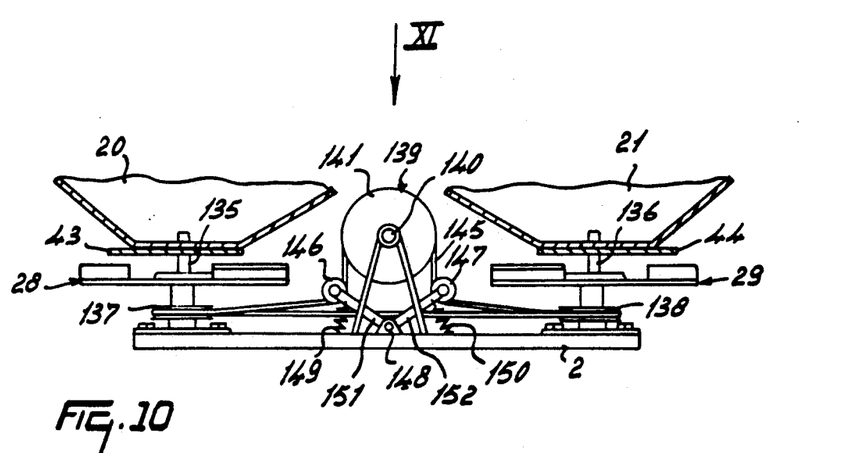
FIG. 10 shows another embodiment of the transmission mechanism for the spreader of FIGS. 1 and 2.
Figure 11:
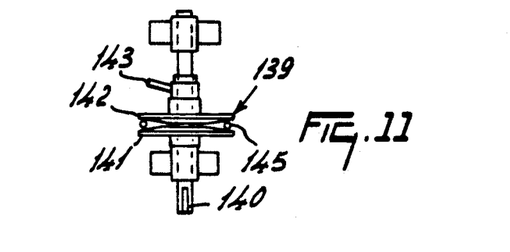
FIG. 11 is a schematic plan view of part of the transmission mechanism of FIG. 10 taken in the direction of the arrow XI in FIG. 10.

FIGS. 10 and 11 show a different arrangement for driving the distribution members 28 and 29. In this embodiment the distribution members 28 and 29 are arranged on vertical shafts 135 and 136 respectively, each having a pulley 137 and 138 respectively. These pulleys 137 and 138 are located beneath the distribution members 28 and 29. At the centre of the distributor there is a drive pulley 139 which is fastened to an input shaft 140, like the shaft 38 of the first embodiment and the shaft 111 of the second embodiment. The pulley 139 has flanges 141 and 142 between which a V-shaped groove is formed, and these flanges are relatively axially movable along the shaft 140 by means of an adjusting mechanism 143 (not shown in detail). By changing the distance between the flanges 141 and 142 the effective diameter of the pulley is varied. Thus a driving rope or belt 145, which is run over guide rollers 146 and 147 can drive the pulleys 137 and 138 with a variable speed, with the same speed as the shaft 140. In order to compensate for the change of effective diameter of the pulley 139 with respect to the length of the rope 145, the guide rollers 146 and 147 are mounted on arms 151 and 152 respectively, which are pivotable about a shaft 148 under the action of springs 149 and 150 respectively. Thus the guide rollers 146 and 147 constitute tensioning rollers constantly keeping the driving rope 145 taut. The transmission mechanism of FIGS. 10 and 11 permits a stepless speed variation, within limits, of the distribution members 28 and 29. Therefore, the speed of the distribution members 28 and 29 can be set very accurately to keep the width of spread of the material accurately within given limits.

Figure 12:
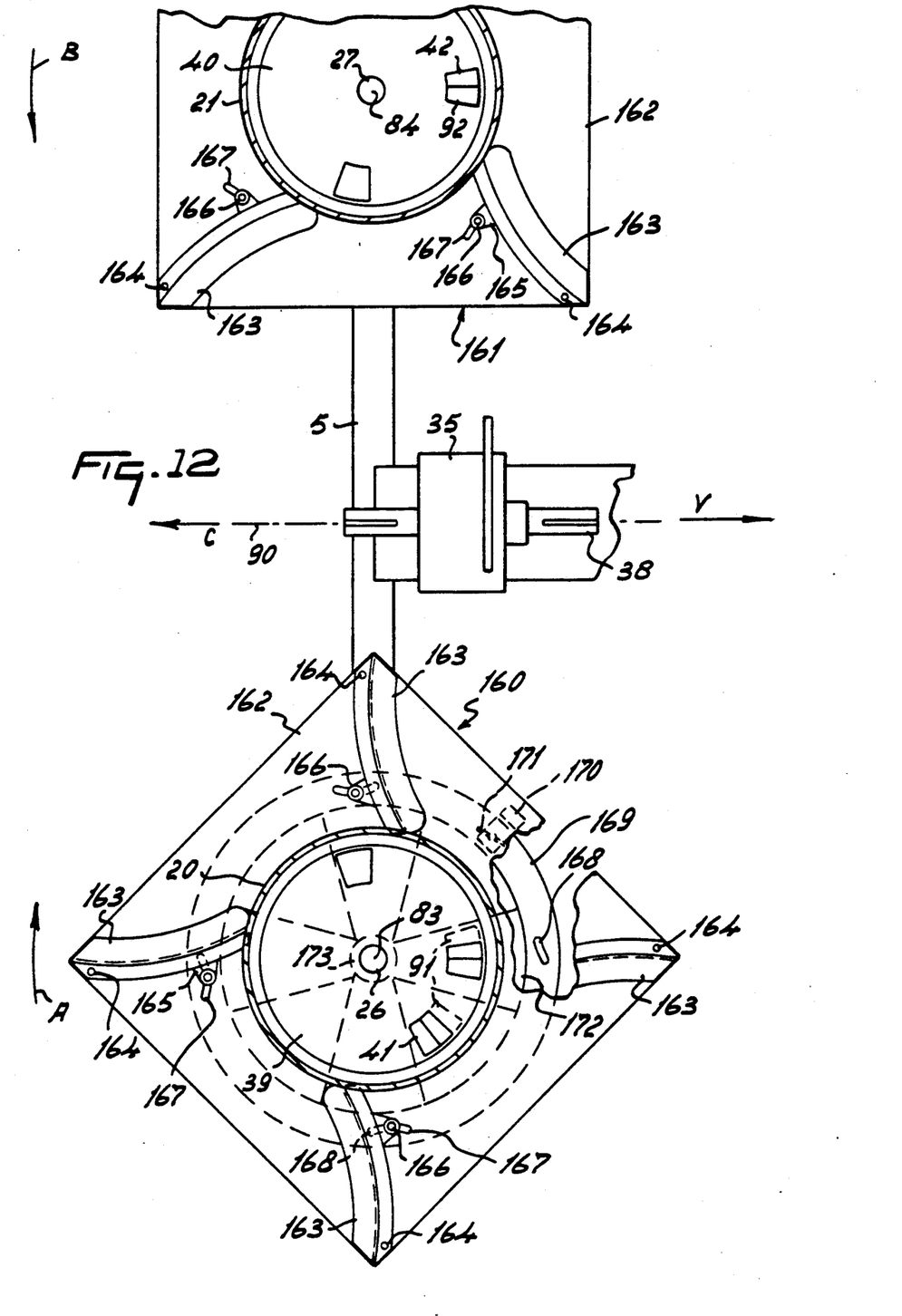
FIG. 12 is an enlarged plan view showing an alternative construction for distribution members of the spreader of FIGS. 1 and 2.

In FIG. 12 parts corresponding with those of FIGS. 1 and 2 are designated by the same reference numerals as in those Figures. In the embodiment shown in FIG. 12, two distribution members 160 and 161 are fastened to the vertical shafts 26 and 27 respectively. Each distribution member 160 and 161 comprises a square plate 162, each plate being provided with four ejection blades 163. The ends of the blades 163 away from the shaft 26 and 27 are located at the corners of the plates 162. Each of the blades 163 is pivotally connected to the plate 162 by means of a pivotal shaft 164. The pivotal shaft 164 is located near the outer end of the blade 163 and therefore near the corner of the plate 162. On the trailing side with respect to the direction of rotation A or B respectively, each of the blades 163 has a lug 165 carrying a pin 166. This pin 166 can move in a slot 167 in the plate 162 and in a slot 168 in a ring 169. The ring 169 is beneath the plate 162 and can be turned with respect to the plate 162 about the centerline 83 of the shaft 26 and the centerline 84 of the shaft 27 respectively. Each of the rings 169 of the distribution members 160 and 161 can be fixed in position with respect to its plate 162 by a fixing member 170 having a wing nut 171. By turning the blades 163 about the pivotal shafts 164 the orientation of the blades 163 on the plates 162 can be changed so that the blades 163 will occupy a different orientation relative to the rotary axis 83 and 84 respectively of the distribution members. By varying the position of the blades, the direction of spreading can be slightly altered. The position variation of the blades about the rotary axes can result in ejection of a given kind of material over a greater or smaller distance while the speed of the distribution members remains the same. The direction of the spread is also affected. In the embodiment shown the position variation of the blades 163 is such that the four blades of a distribution member can be displaced together and be fixed in a given orientation relative to the rotary axis of the distribution member so that each blade of the plate 162 acts upon the material in the same manner. For this variation in unison of the blade orientations it is necessary only to turn the ring 169 about the axes 83 and 84 respectively and to fix it in the new position using the fixing member 170. The slots 168 in the ring 169 are positioned so that turning of the ring 169 results in a position variation of the pin 166 so that the blades will turn about the pivotal shafts 164. The pins 166 are also guided by the slots 167 in the plates 162 so that the desired turn of the blades about the pivotalshafts 164 is ensured. Each ring 169 is connected by four spokes 172 with a hub 173, which is rotatable on the shaft 26 or 27.

In the embodiment of FIG. 12 the distribution members 160 and 161 are not positioned symmetrically with respect to the vertical central plane 90 as are the distribution members 28 and 29 in FIG. 2. In the embodiment of FIG. 12 the distribution members 160 and 161 have identical shapes, but as is shown in the Figure the distribution member 160 is offset by 45° with respect to the distribution member 161. As a result, the blades of the distribution member 160 will eject the material approximately in the direction C (see FIG. 2) at other instants than the blades 163 of the distribution member 161. Thus in approximate alternation a blade of one distribution member and subsequently a blade of the other distribution member will eject a quantity of material. This will have a favorable effect on the uniformity of the distribution of material.

Although as shown in FIG. 12 the orientation of the blades on the plates of the distribution members relative to the rotary axes can be varied by turning the blades about a pivotal shaft located near the outer ends of the blades, this variation may be obtained in a different manner.

Figure 13:
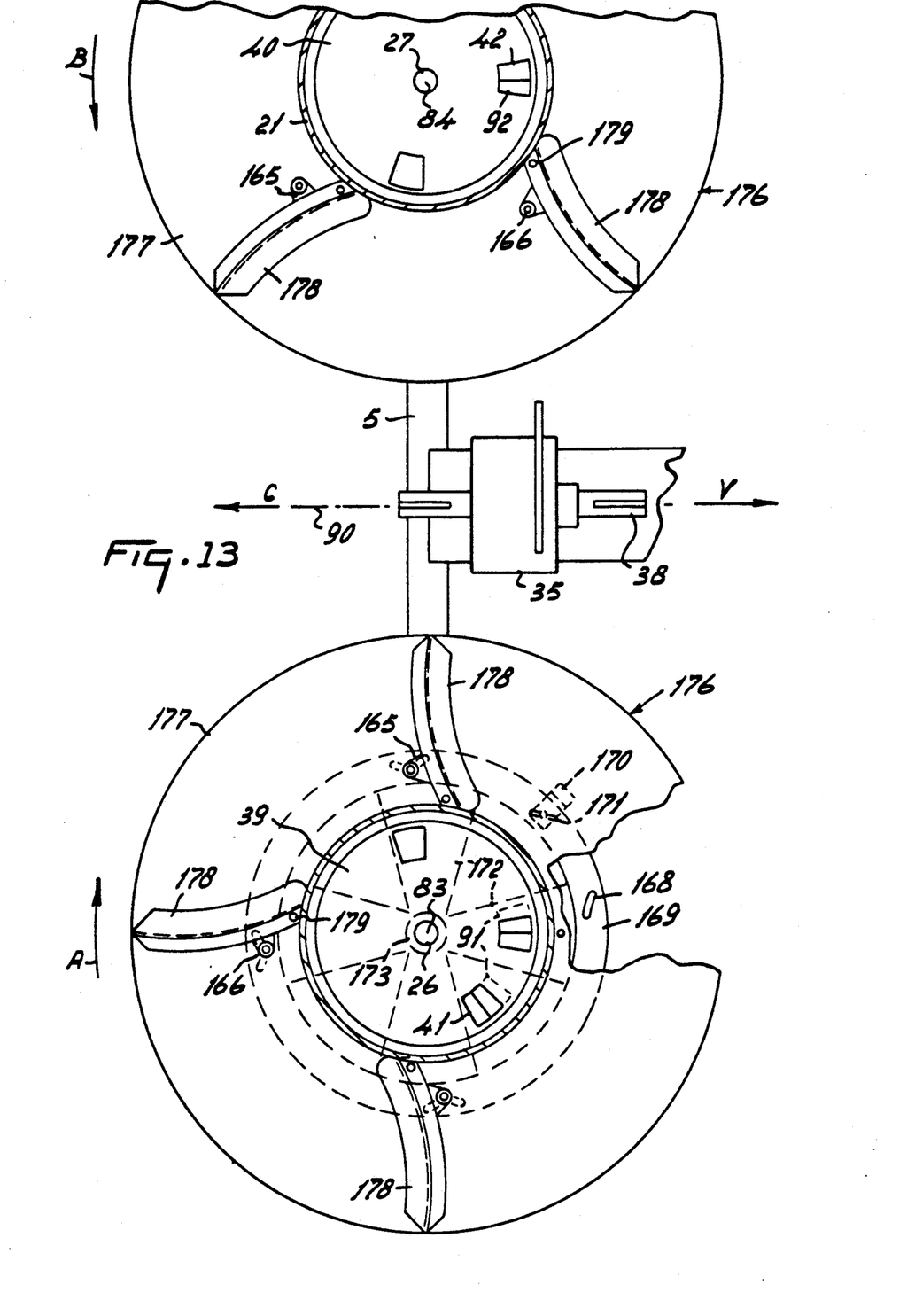
FIG. 13 is a plan view of a further embodiment of the distribution members.

FIG. 13 shows an embodiment having distribution members 176 mounted on shafts 26 and 27. In this embodiment, each distribution member 176 comprises a circular plate 177 provided with four blades 178. The blades 178 are pivotable about pivotal shafts 179, which are arranged near the radially inner ends of the blades. As in the embodiment shown in FIG. 12, the blades are provided with lugs and pins co-operating with slots in the plate 177 and in the ring 169. The lugs and pins of the blades and the slots in the plate and the ring are identical to those of the preceding embodiment and are therefore designated by the same reference numerals. With the pivotal shafts 179 located near the radially inner ends of the ejection blades, adjustment of the blades with respect to the shaft of the distribution member results in displacement of the radially outer end of each blade. The position variation of the blades with respect to the rotary axis of a distribution member is particularly useful in a distributor in which two distribution members spread the material across the same sector as is indicated in the embodiments shown.

Figure 14:
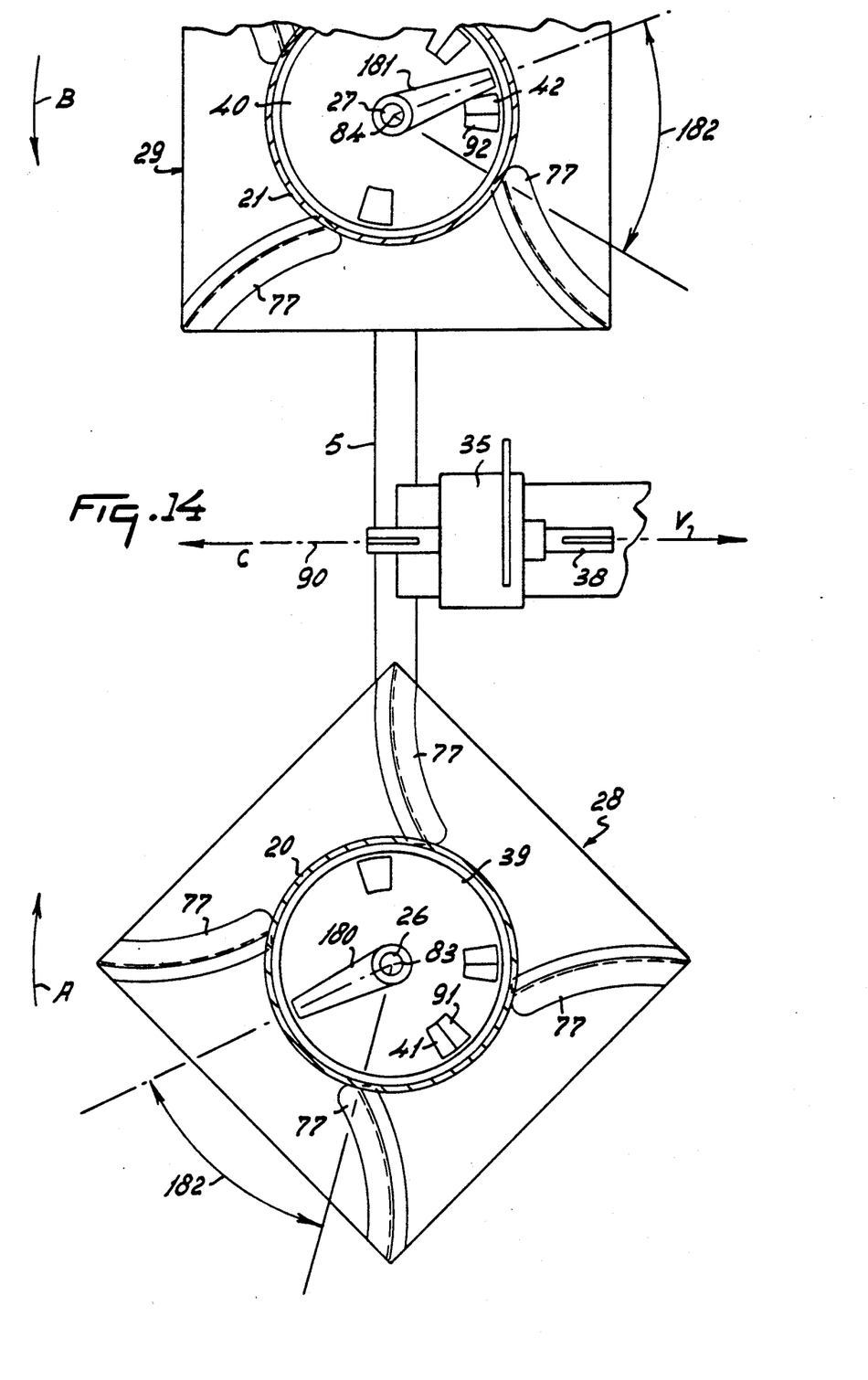
FIG. 14 shows another construction for the parts visible in FIG. 12.

FIG. 14 shows an embodiment corresponding largely with the embodiment shown in FIG. 2. In the embodiment shown in FIG. 14, the shafts 26 and 27 of the distribution members 28 and 29 respectively are each provided with a displacer in the form of a blade 180 or 181. These blades 180 and 181 are located as the lower parts of the funnel portions 20 and 21 and extend radially from the shafts 26 and 27 to near the peripheries of the lower ends of the funnel portions 20 and 21. The blades 180 and 181 are a short distance of, for example, one mellimeter, above the bottom walls 39 and 40. The blades 180 and 181 are rigidly connected with the shafts 26 and 27 respectively and rotate with them and with the distribution members at the same speed about the rotary axes 83 and 84 respectively. The blades 180 and 181 are arranged so that they lead one of the ejection blades 77 by an angle 182 of about 50°. The angle 182 is measured between the center line of the displacer blade and the radial line passing through the radially inner end of the ejection blade as indicated in FIG. 14. The blade 180 is offset by 180° from the blade 181 so that the blades 180 and 181 approach the vertical plane 90 alternately.

During distribution of material, the displacer blades 180 and 181 loosen the material along the bottom wall so that, immediately after the passage of a displacer blade, the material will flow more readily through the outlet ports 41 and 42. Owing to this temporarily enhanced flow of material from the hopper through the outlet ports, the ejection blade trailing the blade 180 or 181 by the angle 182 will receive more material from the outlet port than will the other ejection blades of the distribution member. Because the blades 180 and 181 are relatively offset by 180° an ejection blade of one distribution member will spread more material alternately with an ejection blade of the other distribution member. This results in a uniform distribution pattern from the two distribution members 28 and 29. Therefore, the displacer blades are particularly useful in devices having two distribution members spreading the material across the same sector. Although in this embodiment each of the distribution members 28 and 29 has four ejection blades, there may be a different number of ejection blades. In particular, when displacer blades such as 180 and 181 are employed, a distribution member may have only one ejection blade, lagging by the angle 182 with respect to the displacer blade. The angle 182 is again preferably about 50°, but may vary in dependence upon the shape of the distribution member, the location of the outlet ports and the kind of material to be spread. The angle 182 should not be larger than about 90° and not smaller than about 30°.

When a displacer blade is used with a distribution member of moderate diameter having moderately long ejection blades, it may be advantageous to use at least two ejection blades. If there are two, the second ejection blade should then be offset by 180° with respect to the ejection blade co-operating with the displacer blade. As an alternative, the distribution member may have a single ejection spout co-operating with a displacer blade. The ejection spout may then communicate with a central, cup-shaped part of the distribution member capturing material flowing from an outlet port.

Figure 15:
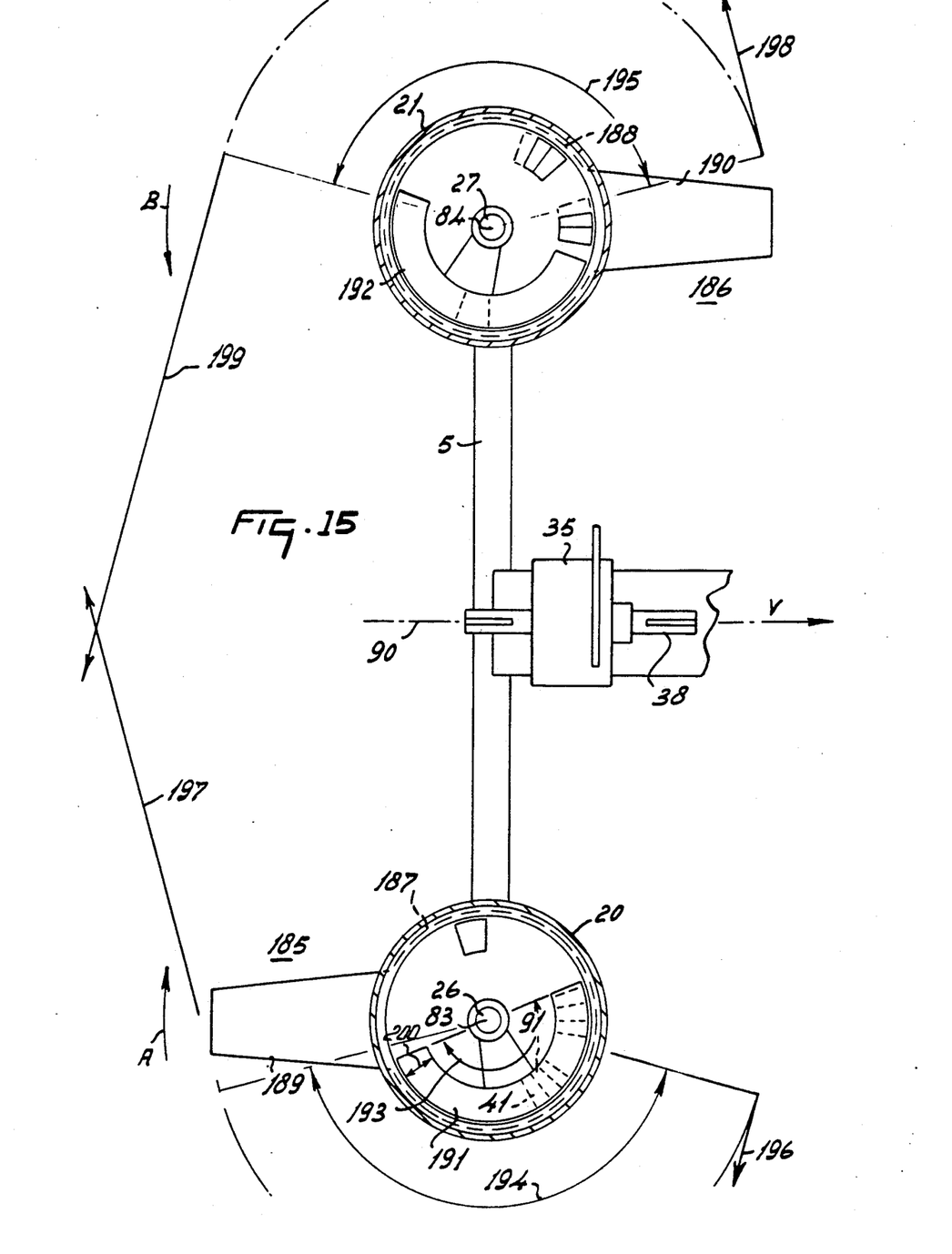
FIG. 15 is a plan view of a further embodiment of the distribution members.

FIG. 15 shows an embodiment comprising two distribution members having each an ejection spout. In this embodiment the ejection spouts do not co-operate, however, with an advancing blade as in the construction just referred to, but with a closing mechanism. The parts of the distributor shown in FIG. 15 and corresponding with those of FIG. 2 are designated by the same reference numerals as in FIGS. 1 and 2. In the embodiment shown in FIG. 15 the distribution members 185 and 186 are mounted on the shafts 26 and 27 respectively. Each distribution member 185 or 186 comprises a cup-shaped portion 187 or 188 respectively (not shown in detail), the diameter of which is similar to the diameter of the bottom walls 39 and 40 of the hopper. Each of these cup-shaped portions 187 and 188 is provided with an ejection spout 189 and 190 respectively. The shafts 26 and 27 are provided with closing plates 191 and 192 respectively. These closing plates 191 and 192 co-operate with the outlet ports 41 and 42 respectively so that material flows out of the funnel portions 20 and 21 to the distribution members 185 and 186 only when it can pass directly to the ejection spouts to be spread across sectors corresponding with the sectors shown in FIG. 3, where each of the distribution members can spread the material. Each closing member 191 or 192 subtends an angle 193 of 180° at the rotary axis 83 or 84 respectively. The closing plates 191 and 192 end at the trailing edges of the ejection spouts 189 and 190 respectively and extend away therefrom to the rear, with respect to the directions of operative rotation A and B. Therefore, after an ejection spout has passed by the outlet ports 41 and 42 these ports will be closed. In this embodiment, in which the closing plates 191 and 192 subtend an angle of 180° at the rotary axes of the distribution members, the outlet ports are closed for one half of each revolution of the distribution member. After the closing plates have passed the outlet ports, the material can again flow out to the distribution member. The material can reach the distribution member so that a uniform transfer to the ejection spout is obtained so that the material can be uniformly spread across the desired sector 194 and 195 respectively. By closing the outlet ports after the passage of an ejection spout no material will accumulate in the central, cup-shaped portion of the distribution member 185 and 186 respectively, which would affect the flow of material toward the ejection spout. It is thus furthermore ensured that the material will be spread only across the desired sector 194 or 195. The ejection spouts 189 and 190 of the distribution members 185 and 186 respectively are offset by 180° from one another so that during their rotation they alternately spread the material across the sector 194 and 195 respectively. In this way a uniform distribution pattern is obtained.

A closing member lagging with respect to the ejection spout for one or more outlet ports may also be used with a distribution member having two ejection spouts or other ejection members, for example, ejection blades. Then the closing member lagging with respect to the ejection member will subtend an angle of less than 180° at the rotary axis of the distribution member. When two ejection spouts are used, a closing member co-operating with each ejection spout may subtend an angle of about 90°. A closing member for one or more outlet ports trailing behind an ejection spout or an ejection blade may also be used with a distribution member having a flat plate on which one or more ejection blades are arranged as in the preceding embodiments.

The angle subtended by the closing member may vary in accordance with the shape and rotary speed of the distribution member and in accordance with the shape and location of the outlet ports. However, the closing member will meet the radially inner part of the ejection spout or blade as shown in FIG. 15 for the closing members 191 and 192 with respect to the ejection spouts 189 and 190.

In the embodiment shown in FIG. 15 the ejection spout 189 will have spread material across the sector 194 when it reaches the position shown in the Figure. In this position, after a small turn in the direction of the arrow A the closing member 191 will uncover the port 41 so that material can flow out of the hopper to be captured by the ejection spout during its further rotation in the direction of the arrow A so that the material is again spread from the line 196 of the sector 194. The ejection spout will receive material for a period of time sufficient for the spout to eject material up to the boundary line 197 of the sector 194. As shown in FIG. 15, the ejection spout 190 is in a position in which the closing member is just about to block the outlet port 42 and the ejection spout will spread material across the sector 195 within the boundary lines 198 and 199. Owing to the relatively offset positions of the ejection spouts 189 and 190 they will alternately spread the material so that a uniform distribution pattern is obtained. The width 200 of the closing members 191 and 192 is great enough to cover the outlet ports fully.

While various features of the spreaders described and illustrated in the drawings, are set forth in the following claims as inventive features, it is to be understood the invention is not necessarily limited to those features and may include all features which have been disclosed both individually and in various combinations.

Having disclosed our invention, what we claim as new and desire to secure by Letters Patent of the United States is:

1. A spreader for spreading granular and/or powdery material comprising a frame, a hopper, feeding means from said hopper and at least two distribution members rotatably supported below said hopper, each said member being rotatably about an upwardly extending shaft, each said distribution member comprising a plate with ejection blades, a displacer connected to each said distribution member and said displacer being positioned to lead at least one of said blades therein with respect to the direction of operative rotation of said plate and adapted to enhance temporarily the flow of material from said feeding means, whereby the flow of material from said feeding means during operation is temporarily enhanced by each said displacer and the temporarily increased flow passes to its respective said distribution member to be ejected by said one blade, each displacer being positioned relative to its respective said distribution member to temporarily enhance the flow of material thereto alternatively with the other said displacer, speed adjusting means carried by the spreader associated with each distribution member for simultaenously controlling the relative velocity of material ejected from each said distribution member causing it to fall substantially within a predetermined area, said feeding means, said distribution members and said adjusting means so constructed and arranged that said areas coincide with one another throughout.

2. A spreader as claimed in claim 1, in which each said displacer comprises a blade element that extends from the rotary shaft of said plate to adjacent a wall of said hopper.

3. A spreader as claimed in claim 2, in which each said element extends rectilinearly away from said shaft.

4. A spreader as claimed in claim 1, in which each said displacer is located directly above the bottom of said hopper and said bottom has at least one outlet port.

5. A spreader as claimed in claim 4, in which each said displacer is inclined at about 50° to a radial line passing through the radially inner end of an ejection blade that trails said displacer.

6. A spreader for spreading granular and/or powdery material comprising two adjacent rotatable distribution members which are symmetrically identical and are disposed at the same level, means for rotating said distribution members about upwardly extending axes, said axes being disposed symmetrically relative to a vertical plane which contains the longitudinal axis of the spreader, feeding means positioned to supply material to said distribution members whereby each of said two distribution members receives material at a location spaced forward of a plane containing said upwardly extending axes and within an arc extending forwardly from the adjacent said upwardly extending axis, the major portion of each said arc being on the outboard side of a forwardly directed plane containing the adjacent said upwardly extending axis, driving means connected to rotate said distribution members in relative opposite directions so portions of said distribution members nearest one another move generally in a forward direction and material is ejected from said distribution members during operation commencing from the outboard moving portions of said distribution members in a generally rearward direction, means simultaneously adjusting said feeding means to feed a selected amount of material to each of said distribution members and means mounted on the spreader for selectively changing each distributor's r.p.m. simultaneously to regulate the size of the areas treated by the respective distribution members, said feeding members, said distribution members and said adjusting means so constructed and arranged that said treated areas are each approximately centered behind their respective distribution member and substantially coincide with each other throughout their widths.

7. A spreader as claimed in claim 6, wherein each said arc is about 70°.

8. A spreader for spreading granular and/or powdery material comprising two side-by-side rotatable distribution members which are symmetrically identical and are disposed at the same level, means for rotating said distribution members about upwardly extending axes, said axes being symmetrical relative to a vertical plane containing the spreader's longitudinal axis, each said means for rotating said distribution members connected to to change-speed means mounted on the spreader for simultaneously changing their respective rotational speeds, feeding means positioned to supply material to each said distribution member whereby each said distribution member receives material at a location laterally offset from the respective rotary axis of that distribution member, said means for rotating said distribution members adapted to rotate said distribution members in relatively opposite directions so that the portions of said distribution members nearest to one another move in directions generally opposite the directions in which said material is ejected from said distribution members during operation, means adjusting said feeding means to feed material to each of said distribution members and to govern the density of material received in areas treated by the respective said distribution members, said feeding means, said distribution members and said adjusting means so constructed and arranged that said treated areas are approximately centered behind their respective distribution member and coincide through their widths except for relatively small lateral outboard areas where they do not coincide.

9. A spreader for spreading granular and/or powdery material which is connectable to a vehicle at its forward side and broadcasts said material from its rear side, the spreader comprising two side-by-side rotatable distribution members which are symmetrically identical and are disposed at the same height relative to the underlying ground, means for rotating said distribution members about upwardly extending axes, said axes being disposed symmetrically relative to a vertical plane containing the spreader's longitudinal axis, feeding means positioned to supply the material to said distribution members whereby each of said distribution members receives material at a location laterally offset from the respective rotary axis of that distribution member, said means for rotating said distribution members connected to rotate said distribution members in relative opposite directions whereby those portions of said distribution members nearest one another move in directions generally opposite to the directions in which material is broadcast from said distribution members during operation, means adjusting said feeding means simultaneously to feed material to each of said distribution members and means mounted on said spreader to change simultaneously the rotational speed of said distribution members to define the size of the areas treated by the respective distribution members, said feeding means, said distribution members and said adjusting means so constructed and arranged that said treated areas are each approximately centered behind the spreader and effectively are substantially coinciding with each other throughout.

10. A spreader for spreading granular and/or powdery material which is connectable to a vehicle at its forward side and broadcasts said material from its rear side, the spreader comprising two adjacent rotatable distribution members which are symmetrically identical and are disposed at the same height relative to the underlying ground, means for rotating said distribution members about upwardly extending axes, said axes being symmetrical relative to a vertical plane containing the spreader's longitudinal axis, feeding means positioned to supply material to said distribution members whereby each of the two distribution members receives material at a location laterally offset from the respective rotary axis of that distribution member wherein said feeding means of each distribution member is spaced forward of a plane containing said upwardly extending axes and within an arc extending forwardly from the adjacent said upwardly extending axis and being substantially on the outboard side of a forwardly directed plane containing the adjacent said upwardly extending axis, said rotating means connected to rotate said distribution members in relative opposite directions whereby portions of said distribution members nearest one another move in directions opposite the direction in which material can be ejected from said distribution members during operation, means adjusting said feeding means to feed the same amount of material simultaneously to each of said distribution members and to cause each said distribution member to commence ejecting material on its outboard side, and means to change the r.p.m. of said distribution members mounted on the spreader to regulate the size of the areas treated by the respective distribution members, said feeding members, said distribution members and said adjusting means so constructed and arranged that said treated areas are each approximately centered behind their respective said distribution members and substantially coincide with one another thorughout.

11. A spreader for spreading granular and/or powdery material comprising two adjacent rotatable distribution members which are symmetrically identical having upwardly extending axes of rotation and being disposed at the same height relative to the underlying ground, means for rotating said distribution members mounted on the spreader which includes change-speed means for each said distribution member for changing its rotational speed and governing the distance material is ejected from said distribution members to govern the size of the areas treated by the respective distribution members, feeding means positioned to supply material to said distribution members whereby each of the two distribution members receives material at a location laterally offset from the respective rotary axis of that distribution member, said means for rotating connected to rotate said distribution members in relative opposite directions whereby portions of said distribution members nearest one another move in directions generally opposite the direction in which material is broadcast from said distribution members during operation, said material commencing to be broadcast from the outboard side of each said distribution member, means adjusting said feeding means simultaneously to feed material to each of said distribution members and to govern the density of material received on the areas treated by the respective distribution members, said feeding means, said distribution members and said adjusting means so constructed and arranged that said treated areas are each approximately centered behind their respective said distribution member and coincide substantially with each other throughout the greater part of their widths.

* * * * *